United States Patent [19]

Nason

[11] Patent Number: 5,266,266
[45] Date of Patent: Nov. 30, 1993

[54] SPECIMEN TEST UNIT

[76] Inventor: Frederic L. Nason, 941 Avenida Acaso, Camarillo, Calif. 93010

[21] Appl. No.: 810,692

[22] Filed: Dec. 19, 1991

Related U.S. Application Data

[63] Continuation-in-part of Ser. No. 625,759, Dec. 10, 1990, Pat. No. 5,078,968, which is a continuation of Ser. No. 153,951, Feb. 9, 1988, Pat. No. 4,978,504.

[51] Int. Cl.$^5$ ............................................. G01N 1/02
[52] U.S. Cl. ..................................... 422/58; 128/759; 128/771; 422/61; 422/102; 435/295; 604/1; 604/2; 604/3
[58] Field of Search ............... 422/56, 57, 58, 61, 422/100, 101, 102; 435/295, 296, 810; 128/759, 771; 604/1-3; 401/196, 198, 132; 206/209

[56] References Cited

U.S. PATENT DOCUMENTS

| | | | |
|---|---|---|---|
| 2,490,168 | 2/1947 | Strauss | 604/2 |
| 2,510,490 | 9/1947 | Ager | 604/1 |
| 3,004,681 | 9/1959 | Jinkens et al. | 215/227 |
| 3,163,160 | 11/1962 | Cohen | 128/759 |
| 3,324,855 | 1/1965 | Heimlich | 604/3 |
| 3,450,129 | 7/1966 | Avery et al. | 128/759 |
| 3,495,917 | 2/1970 | Truhan | 401/132 |
| 3,640,268 | 2/1972 | Davis | 128/759 |
| 3,674,007 | 7/1972 | Freis | 604/1 |
| 3,773,035 | 11/1973 | Aronoff | 435/295 |
| 3,776,220 | 12/1973 | Monaghan | 128/759 |
| 3,792,699 | 2/1974 | Tobin et al. | 435/295 |
| 3,883,396 | 5/1975 | Thomas, Jr. et al. | 128/759 |
| 3,890,204 | 6/1975 | Avery | 128/759 |
| 3,890,954 | 6/1975 | Greenspan | 455/45 |
| 3,913,564 | 10/1975 | Freshley | 128/759 |
| 3,915,806 | 10/1975 | Horlach | 435/295 |
| 3,918,435 | 11/1975 | Beall et al. | 435/295 |
| 3,923,604 | 12/1975 | Monaghan | 435/295 |
| 3,954,563 | 5/1976 | Mennen | 435/295 |
| 3,958,571 | 5/1976 | Bennington | 401/196 |
| 4,014,746 | 3/1977 | Greenspan | 435/295 |
| 4,014,748 | 3/1977 | Spinner et al. | 435/295 |
| 4,059,404 | 11/1977 | Schuster et al. | 128/760 |
| 4,175,008 | 11/1979 | White | 435/295 |
| 4,184,483 | 1/1980 | Greenspan | 128/759 |
| 4,196,167 | 4/1980 | Olsen | 422/61 |
| 4,223,093 | 9/1980 | Newman et al. | 435/295 |
| 4,300,910 | 11/1981 | Pannwitz | 436/102 |
| 4,311,792 | 1/1982 | Avery | 435/30 |
| 4,312,950 | 1/1982 | Snyder et al. | 435/295 |
| 4,340,670 | 7/1982 | Mennen | 435/25 |
| 4,353,868 | 10/1982 | Joslin et al. | 422/101 |
| 4,355,113 | 10/1982 | Mennen | 435/295 |
| 4,387,725 | 6/1983 | Mull | 128/759 |
| 4,409,988 | 10/1983 | Greenspan | 128/759 |
| 4,562,043 | 12/1985 | Mennen et al. | 422/56 |
| 4,586,604 | 5/1986 | Alter | 128/759 |
| 4,604,360 | 8/1986 | Hounsell | 435/287 |
| 4,635,488 | 1/1987 | Kremer | 73/864.72 |
| 4,653,510 | 3/1987 | Koll | 435/295 |
| 4,707,450 | 11/1987 | Nason | 435/295 |
| 4,770,853 | 9/1988 | Bernstein | 422/58 |
| 4,813,432 | 3/1989 | Saint Amand | 128/749 |

FOREIGN PATENT DOCUMENTS 0058008 1/1982 European Pat. Off. .
0155747 10/1985 European Pat. Off. .

*Primary Examiner*—Robert J. Warden
*Assistant Examiner*—Laura E. Collins
*Attorney, Agent, or Firm*—Kelly, Bauersfeld & Lowry

[57] ABSTRACT

An improved specimen test unit is provided for use in the collection and analysis of a biological specimen or the like. The test unit includes a swab member having a hollow shaft closed at a rear end by a break-off nib, and a swab tip at a front end for collecting a selected specimen. The swab shaft rear end is carried by a housing base, with the break-off nib extending into a reagent chamber having a selected reagent therein. The housing base is sufficiently deformable to break the nib and thereby permit reagent delivery through the swab shaft to contact a collected specimen on the swab tip. In a preferred form, a housing cap removably interfits with the housing base to define a specimen chamber with the swab tip enclosed therein, with the housing base and/or cap being conveniently formed from blow molded plastic components.

21 Claims, 4 Drawing Sheets

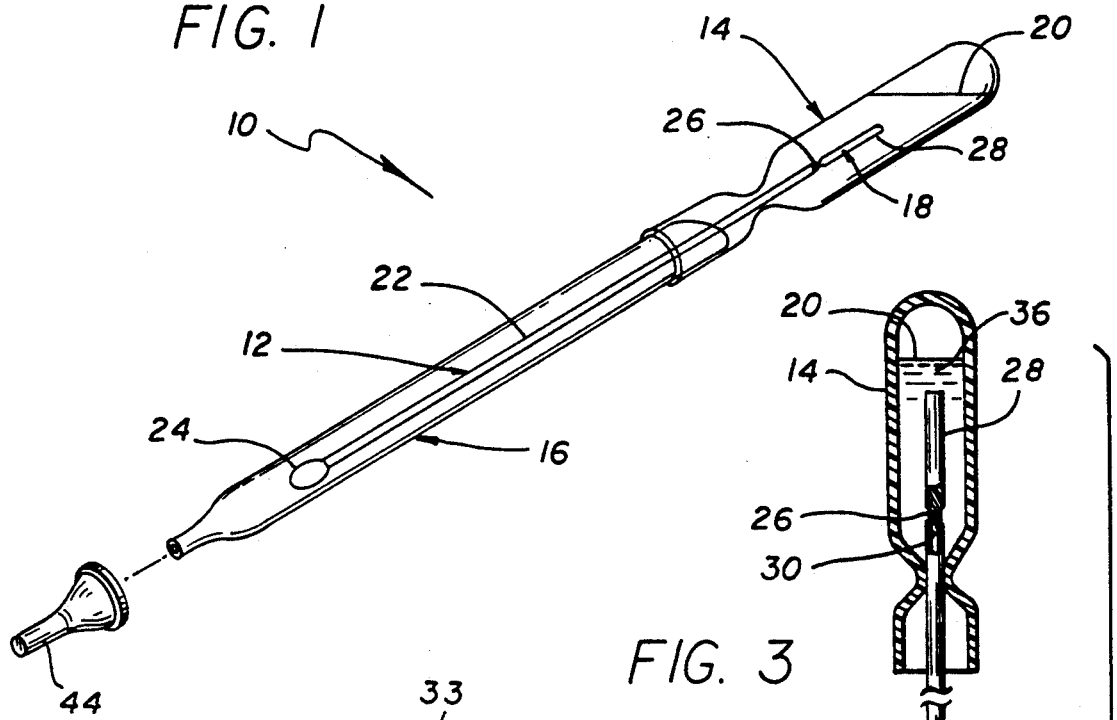
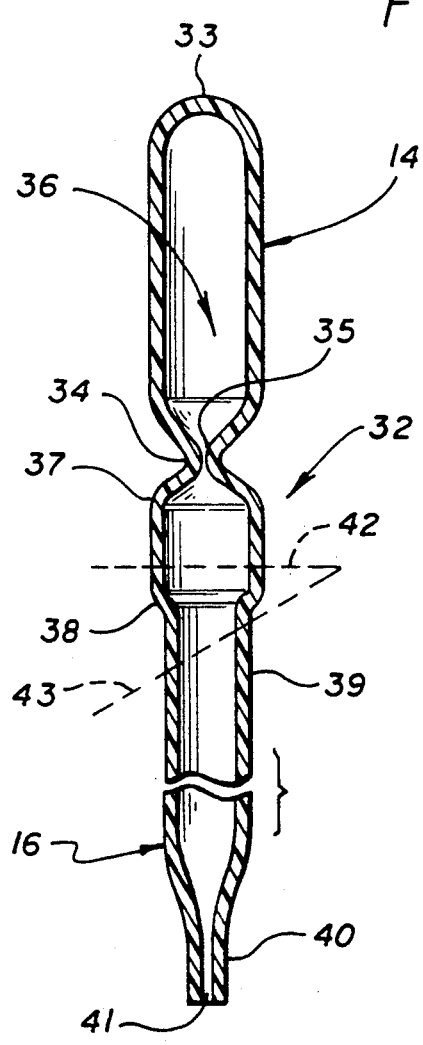
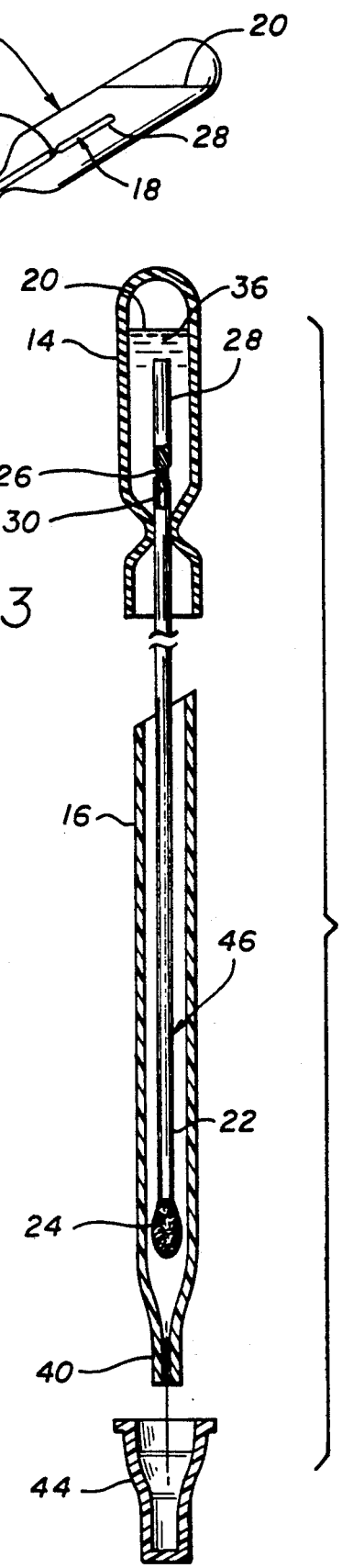

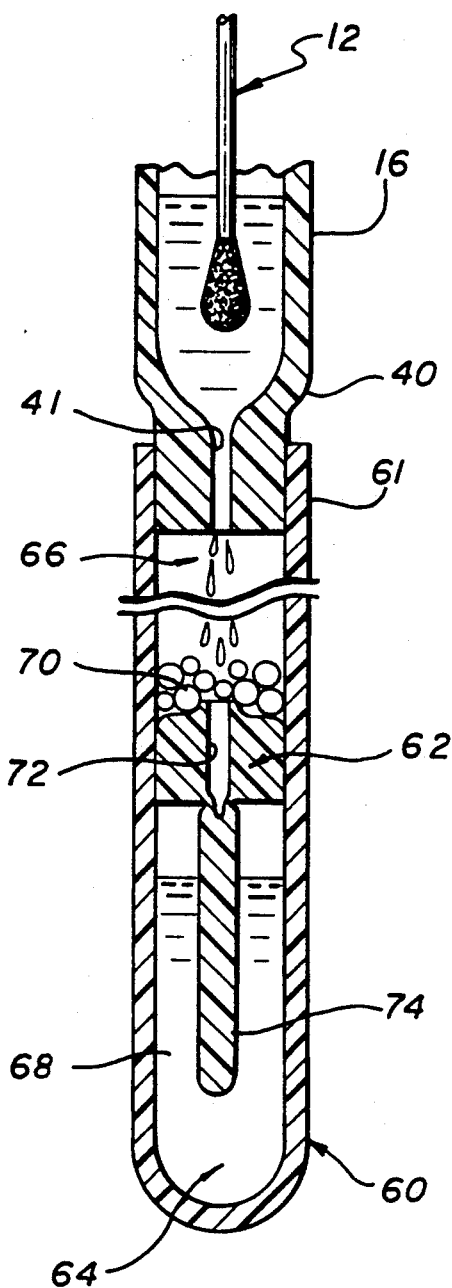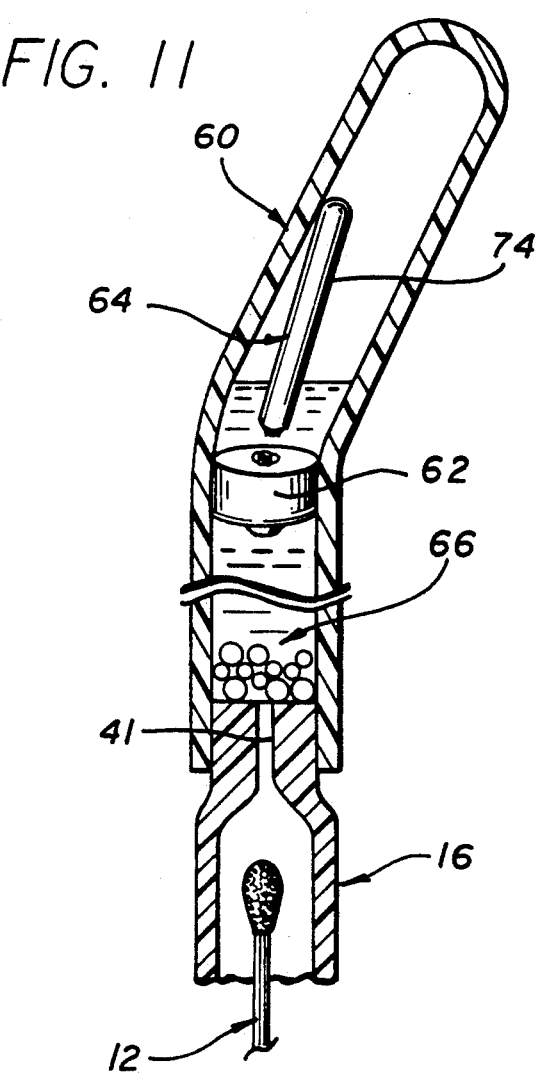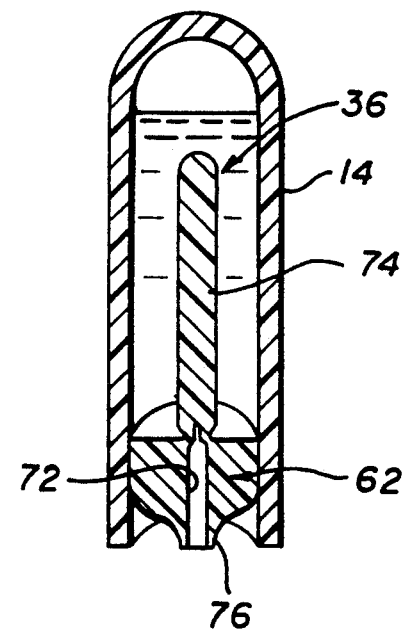

SPECIMEN TEST UNIT

This application is a continuation-in-part of copending application Ser. No. 625,759, filed on Dec. 10, 1990, now U.S. Pat. No. 5,078,968, which in turn is a continuation of copending application Ser. No. 153,951, filed on Feb. 9, 1988, now U.S. Pat. No. 4,978,504, issued Dec. 18, 1990.

BACKGROUND OF THE INVENTION

This invention relates generally to improvements in medical swabs and the like of the type used for collecting biological specimens in the course of performing a variety of medical tests. More particularly, this invention relates to an improved and substantially self-contained specimen test unit having a swab member encased within housing components of blow molded plastic or the like, wherein the test unit includes improved means for handling one or more reagents and for delivering such reagent to the swab tip in the course of performing a medical analysis.

Medical swabs are generally known in the art for use in collecting biological specimens from a patient for further analysis. Such medical swabs commonly comprise a fibrous swab tip at one end of an elongated stick or shaft which is manually handled to contact the swab tip with selected tissue cells or other biological specimen obtained, for example, from within the ear, nose or throat of a patient. As a result, some of the targeted biological specimen adheres to the swab tip which can then be contacted with one or more selected reagents to indicate the presence of infection or other information regarding patient condition. Tests commonly performed with such patient specimens include, by way of example, fluorescent tests, enzymatic tests, monoclonal based tests, agglutination tests, and others.

In accordance with standard techniques, the collected biological specimen is normally transferred from the swab tip to a slide or other laboratory apparatus such as a test tube or the like for contact with the selected reagent and further analysis. However, it is frequently difficult to ensure transfer of a sufficient specimen quantity from the swab tip to the laboratory slide or test tube to ensure accurate test results. Moreover, in many instances, the collected specimen must be transported to a medical laboratory for performance of selected assays, but delays between the time of specimen collection and actual test performance can result in partial or complete drying of the specimen, with a corresponding decrease in test reliability.

Various swab-type collection devices have been proposed in efforts to provide enhanced contact between a specimen and reagent, or, in the alternative, to sustain the specimen during post-collection transport to a medical laboratory. Such swab collection devices have been provided in the form of a compact kit including a fibrous-tipped swab together with one or more reagents for contacting a specimen collected upon the swab tip. In some designs, the reagent is carried by a frangible glass ampoule which is broken at the appropriate time to release a reagent for contacting the specimen on the swab tip. The glass ampoule, however, comprises an additional and relatively costly component to the collection device or kit. Moreover, the glass ampoule produces sharp fragments when broken, wherein the collection device must be designed to prevent the glass fragments from contacting the collected specimen or medical personnel. Alternative swab collection devices have envisioned reagent placement within rupturable cells or compartments formed within a plastic swab housing. In these designs, the reagent cell or compartment is opened at the appropriate time to permit reagent flow into contact with the collected specimen on the swab tip. While this approach avoids the disadvantages associated with glass ampoules, the manufacture of plastic housings with liquid-filled compartments adapted for controlled rupture has been relatively difficult and generally unreliable.

There exists, therefore, a significant and continuing need for further improvements in swab-type specimen test units, particularly with respect to facilitated reagent delivery to a collected specimen on a swab tip, without requiring the use of reagent-containing glass ampoules or rupturable plastic compartments. The present invention fulfills these needs and provides further related advantages.

SUMMARY OF THE INVENTION

In accordance with the invention, a specimen test unit is provided for use in collecting a biological specimen or the like, for example, from a patient. The invention includes a swab member carried by a housing base defining a reagent chamber with a liquid reagent contained therein. The swab member is manipulated quickly and easily while holding the housing base to collect a selected specimen on a swab tip, after which the housing base can be interfitted with a housing cap to cooperatively define a specimen chamber with the swab tip disposed therein. A break-off nib at or on a rear end of the swab member permits reagent delivery from the reagent chamber through a hollow swab shaft to contact the specimen on the swab tip.

In accordance with one preferred form of the invention, the housing base and housing cap are formed from lightweight resilient and deformable plastic components. The preferred components are constructed initially as a unitary blow-molded element which may be separated into the housing base and cap adapted for removably interfitting with each other to define the specimen chamber. An outlet port may additionally be formed in the housing cap for dispensing a portion of the mixed specimen and reagent from the specimen chamber. An auxiliary housing member with one or more additional reagents therein can be mounted on the housing cap for receiving the specimen-reagent mixture transferred through the outlet port.

The swab member includes the hollow swab shaft extending between a swab tip adapted to collect a targeted specimen and the break-off nib. A rear end of the hollow shaft is seated within a seal collar on the housing base to project a short distance into the reagent chamber. The break-off nib is disposed within the reagent chamber and normally prevents reagent flow into the swab shaft. Deformation of the housing base is effective to sever the nib from the swab shaft at a preformed score to open the rear end of the swab shaft and permit reagent flow from the reagent chamber through the swab shaft to the swab tip. In one form, the nib comprises an integral continuation of the swab shaft. In another form, the nib comprises an integral portion of a seal fitting adapted for press-fit mounting into the housing cap with a rear end of the swab shaft seated therein.

In an alternative form, the seal fitting with integrally formed break-off nib is press-fit into a housing base having one open end, with the housing base and seal fitting cooperatively defining a reagent chamber for receiving a liquid reagent or other selected medical fluid. Dispensing of the reagent is permitted by breaking off the nib to open a dispense port formed in the seal fitting. An outboard face of the seal fitting may be contoured to define a drop former tip, such that discrete drops of the reagent can be dispensed by controlled squeezing of the housing base.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is an exploded perspective view illustrating one preferred construction for a specimen test unit embodying the novel features of the invention;

FIG. 2 is an enlarged fragmented vertical sectional view illustrating a unitary blow molded housing element for use in the specimen test unit of FIG. 1;

FIG. 3 is a fragmented and partially exploded vertical sectional view illustrating further construction details of the specimen test unit of FIG. 1;

FIG. 10 is an enlarged fragmented vertical sectional view illustrating a further alternative preferred form of the invention, wherein a housing cap is associated with additional housing components defining a sequence of specimen analysis chambers;

FIG. 11 is a fragmented perspective view depicting use of the embodiment of FIG. 10;

FIG. 12 is a fragmented perspective view of another alternative preferred form of the invention.

DETAILED DESCRIPTION OF THE PREFERRED EMBODIMENTS

Figure 4:
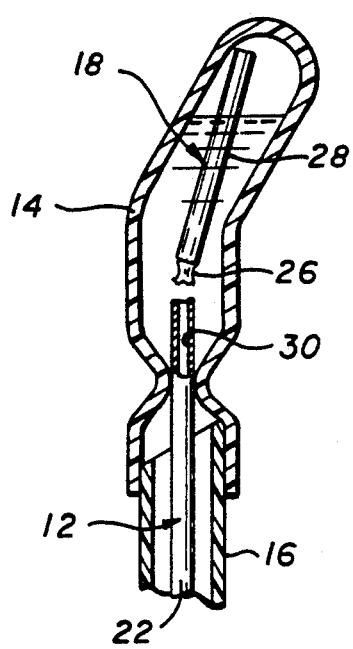
FIG. 4 is an enlarged fragmented vertical sectional view depicting deformation of a housing base to sever a break-off nib from a swab member of the specimen test unit.

As shown in the exemplary drawings, an improved specimen test unit referred to generally in FIG. 1 by the reference numeral 10 is provided for use in collecting a biological specimen or the like and for performing a selected test, such as a medical assay, with respect to the collected specimen. The test unit 10 comprises the combination of a swab member 12 enclosed within interfitting housing components 14 and 16. The swab member 12 includes a break-off nib 18 to permit delivery of a reagent 20 through a hollow swab shaft 22 to contact a collected specimen on a swab tip 24. In addition, the housing components 14 and 16 are adapted for economical and high volume production as blow molded plastic elements.

The improved specimen test unit of the present invention provides a relatively simple and self-contained product for collecting and testing biological specimens such as tissue, cells, body fluid, and the like obtained from a patient. The test unit provides means for substantial and thorough contact of the collected specimen with one or more selected reagents. In some forms, the test unit is entirely self-contained to permit the selected medical assay to be performed without requiring additional test apparatus such as laboratory slides, test tubes, etc. In other forms, the test unit is adapted to facilitate transfer of a collected specimen to a laboratory slide or other laboratory apparatus for further analysis. Examples in which the specimen test unit of the present invention may be used include, but are not limited to, fluorescent tests, enzymatic tests, monocolonal based tests, agglutination tests, and others.

As shown in detail in FIGS. 1–5, with respect to one preferred form of the invention, the illustrative specimen test unit 10 constitutes an elongated, relatively thin implement having an overall size and shape for easy manual handling during use. The swab member 12 is shown with the elongated hollow shank or shaft 22 having a front end supporting the swab tip 24 of cotton, Dacron, or other absorbent fibrous material which may be wound or otherwise suitably attached to the hollow shaft. It will be understood, however, that other types of swab tips such as a brush or the like may be used. The swab shaft 22 is formed from a molded plastic or other suitable material to have a relatively stiff but somewhat flexible construction corresponding generally with conventional swabs used in a medical environment.

A rear end of the swab shaft 22 carries the break-off nib 18. More particularly, the rear end of the swab shaft 22 is joined at a reduced diameter score 26 with a solid rod segment 28 formed as a continuation of the swab shaft. A central bore 30 (FIGS. 3–5) defined by the hollow shaft 22 terminates generally at the score 26, whereby the solid rod segment 28 effectively closes the rear end of the swab shaft against fluid inflow.

The swab member 12 is normally positioned within the housing components 14 and 16, with the resultant package being provided as a preassembled and preferably sterile unit. The housing components constitute a housing base 14 formed with a generally cylindrical shape to have one closed end and an opposite open end. The housing base is adapted for sliding, sealed interfit with an elongated and generally cylindrical housing cap 16. Both of these housing components 14 and 16 are conveniently and preferably constructed as lightweight and economical plastic elements.

More specifically, the housing components 14 and 16 are desirably constructed as a unitary blow molded element 32, as viewed in FIG. 2. That is, the unitary element 32 defines the housing base 14 having a closed end 33. From the closed end 33, the housing base extends with a cylindrical geometry to a seal collar 34 of reduced diametric size defining a narrow aperture 35 opening into a reagent chamber 36. From the seal collar 34, the housing base expands to a larger diametric size to define a female housing fitting 37. This fitting 37 is joined integrally to the housing cap 16 by means of a transition shoulder segment 38 which reduces the diametric size of the blow molded element 32 to define an upper end 39 for the housing cap 16. Importantly, this cap upper end 39 has a diametric size for sealed, slide-fit reception as a male fitting into the female housing fitting 37. A lower end 40 of the housing cap 16 is necked down to a smaller diametric size defining a narrow outlet port 41. Alternately, the lower end 40 of the housing cap 16 may be closed off after blow molding, if desired.

The blow molded element 32 is separated into the housing base and cap 14 and 16 by appropriately cutting in the region of the shoulder segment 38. A first cut 42 near a lower and of the fitting 37 separates the base and cap into two discrete components, and a second cut 43 at a position slightly below the shoulder segment 38 permits sealed slide-fit reception of the cap upper end 39 into the fitting 37. The second cut 43 is conveniently formed at an angle, as shown in FIG. 2, to accommodate facilitated slide-fit engagement of the housing base and cap.

The housing base 14 is adapted to receive the liquid reagent 20 into the reagent chamber 36. In this regard, the reagent 20 is placed into the chamber 36 via the aperture 35. After the reagent chamber is appropriately filled, the rear end of the swab shaft 22 is slidably pressed into the aperture 35, in sealing engagement with the seal collar 34. The swab shaft is pressed into and through the aperture 35 to place the score 26 at least a short distance into the reagent chamber 36, as viewed in FIGS. 1 and 3. The housing cap 16 is then fitted over the protruding swab shaft 22 and tip 24, in slide-fit sealed relation with the fitting 37 on the housing base 14. An overcap 44 is conveniently provided in press-fit relation onto the lower end 40 of the housing cap 16 for normally closing the outlet port 41 formed therein.

When use of the specimen test unit 10 is desired, for purposes of collecting a biological specimen or the like, the housing cap 16 is slidably removed from the housing base 14 to expose the protruding swab shaft 22 and the associated swab tip 24. In this configuration, the housing base 14 provides a convenient handle for manual manipulation of the swab member 12 to collect a selected specimen on the absorbent tip 24. After the specimen has been collected, the housing cap 16 is normally reinstalled onto the housing base 14 to enclose the swab tip 24 with the collected specimen thereon. In this configuration, the interfitted housing base and cap 14 and 16 cooperatively define a specimen chamber 46 with the swab tip 24 disposed therein.

Figure 5:
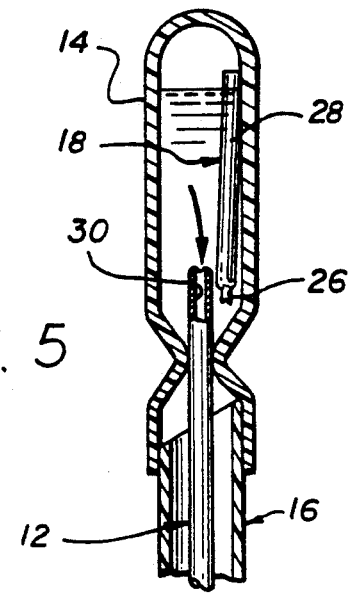
FIG. 5 is an enlarged fragmented vertical sectional view similar to FIG. 4, and illustrating reagent flow through a hollow shaft of the swab member.

As shown in FIGS. 4 and 5, the resiliently deformable plastic material of the housing base 14 permits manual bending of the housing base sufficiently to break off the nib 18 at the rear end of the swab shaft 22. That is, such deformation of the housing base 14 is effective to bend the rod segment 28 relative to the shaft 22 to break the rod segment 28 at the narrow score 26. Such break-off action opens the rear end of the swab shaft 22 for reagent inflow from the reagent chamber 36. A slight application of manual squeeze pressure to the housing base 14 is effective to deliver a substantial portion of the reagent through the hollow shaft 22 for purposes of contacting the collected specimen on the swab tip 24. In this regard, deformation of the housing base 14 sufficient to sever the nib 18 (FIG. 4) will normally deform and compress the reagent chamber 36 to provide substantially immediate reagent delivery when the nib breaks. Such immediate pressure-forced reagent delivery can be prevented or minimized, if desired, by squeezing the housing base 14 to reduce the reagent chamber volume during reagent filling and swab installation, after which the base 14 can be released to apply a slight vacuum to the reagent until nib break-off.

The dispensed reagent contacts the swab tip 24 and the specimen thereon to form a specimen-reagent mixture. When the housing cap 16 is mounted on the housing base 14 before reagent dispensing, the mixture forms a pool within the specimen chamber 46 which may be analyzed directly, or otherwise transferred through the outlet port 41 upon removal of the overcap 44. In this regard, transfer of the specimen and reagent from the specimen chamber 46 can be performed in the manner described and claimed in U.S. Ser. No. 4,978,504, or in copending Ser. No. 625,759, filed Dec. 10, 1990, which are incorporated by reference herein. Alternately, in some instances, it may be preferred to dispense the reagent through the swab shaft 22 to contact the specimen on the swab tip 24, without prior mounting of the housing cap 16 onto the base 14.

Figure 6:
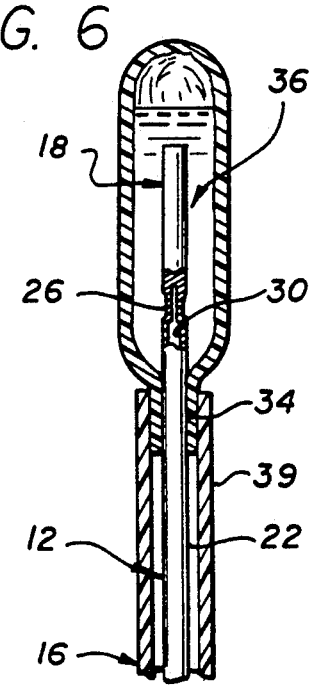
FIG. 6 is an enlarged fragmented vertical sectional view similar to FIGS. 4 and 5 and depicting one alternative preferred form of the invention.

FIG. 6 illustrates one alternative preferred form of the invention, wherein components identical to those shown and described in FIGS. 1-5 are referred to by common reference numerals. In the embodiment of FIG. 6 the overall construction and operation of a modified test unit are the same as the embodiment of FIGS. 1-5, except that the bell-shaped fitting 37 is omitted from the housing base 14. Instead, the upper end 39 of the housing cap 16 is shaped for sealed and slide-fit reception over the narrower diameter seal collar 34. Once again, the break-off nib 18 on the rear end of the swab shaft 22 projects into the reagent chamber 36, and the base 14 is sufficiently deformable to permit the nib 18 to be severed from the swab shaft 22 when reagent dispensing is desired.

Figure 7:
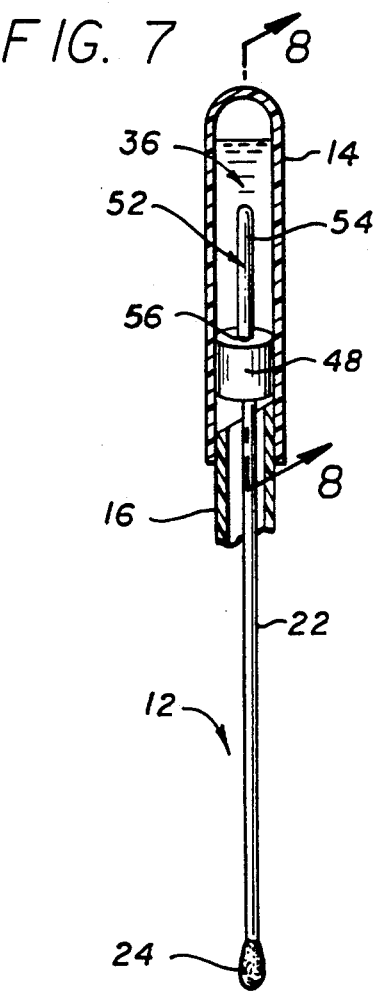
FIG. 7 is a fragmented perspective view illustrating another alternative preferred form of the invention.
Figure 8:
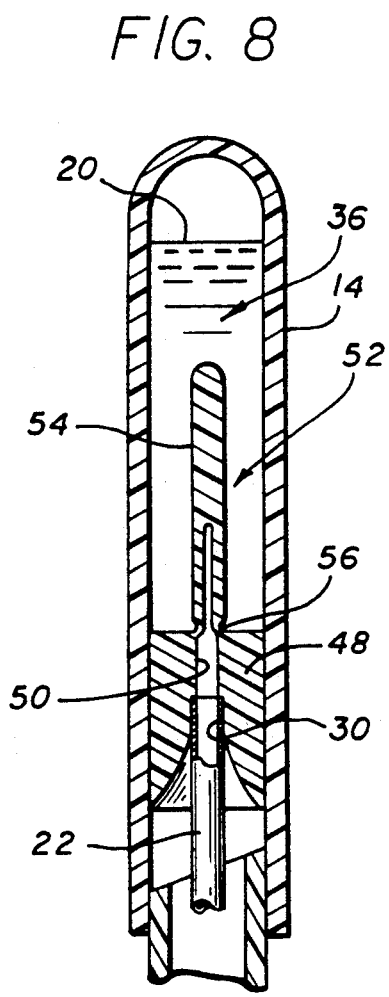
FIG. 8 is an enlarged fragmented vertical sectional view taken generally on the line 8—8 of FIG. 7.
Figure 9:
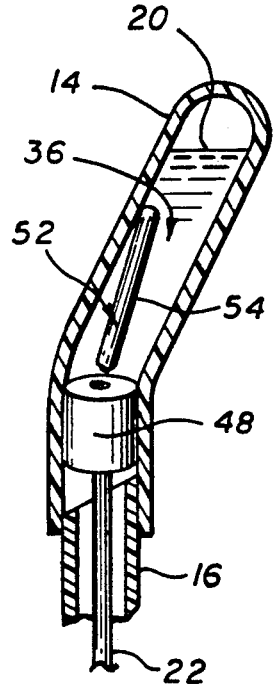
FIG. 9 is a fragmented perspective view depicting deformation of a housing cap to sever a break-off nib, corresponding with the embodiment of FIGS. 7 and 8.

FIGS. 7-9 illustrate another alternative embodiment of the invention, wherein components corresponding in structure or function with those described in FIGS. 1-6 are again identified by common reference numerals. In this embodiment (FIGS. 7-9), a modified housing base 14 has a generally cylindrical, open-ended construction adapted for slide-fit sealed reception of a seal fitting 48 into the open end thereof. The seal fitting 48 can be formed as an injection molded plastic component or the like and normally closes a reagent chamber 36 in the housing base subsequent to filling with a selected reagent 20. The seal fitting includes a central dispense aperture or passage 50 (FIG. 8) having an outboard end which is outwardly flared for easy and self-guided press-fit reception of the open upper end of a hollow swab shaft 22. The central passage 50 in the seal fitting 48 is normally closed by a break-off nib 52 in the form of an extended solid rod segment 54 connected to the seal fitting 48 at an inboard end of the passage 50 via a reduced diameter score 56. A housing cap 30 may be provided for slide-fit engagement with the housing base 14 to enclose the swab 12.

The embodiment of FIGS. 7-9 is utilized in the same manner as described previously with respect to FIGS. 1-6. That is, the housing base 14 and associated housing cap 16 are adapted for slidable reassembly subsequent to collection of a specimen on a swab tip 24 to enclose the specimen and swab tip 24 within a specimen chamber. The housing base 14 can then be deformed sufficiently to break off the rod segment 54 (FIG. 9), and thereby permit reagent delivery through the seal fitting 48 and the swab shaft 22 to the swab tip. If desired, the reagent 20 within the reagent chamber 36 may comprise a first reagent or suitable fixative or other medical liquid which can dissolve a second reagent in dried form disposed within the aperture 50 of the seal fitting 48.

FIGS. 10 and 11 illustrate the structure and function of an auxiliary housing member 60 which can be used in conjunction with the housing cap 16 of FIGS. 1-9 to perform a selected test or assay in a self-contained kit. As shown, the auxiliary housing member 60 has a generally cylindrical construction with one open end 61 sized for slide-fit sealed reception over the lower end 40 of the housing cap 16. A dispense member 62 is press-fit into the interior of the auxiliary housing member 60 to subdivide the housing member into a lower chamber 64 and an upper chamber 66. As shown in FIG. 10, the lower chamber 64 may contain one reagent 68 in liquid form, and the upper chamber 66 may contain another reagent such as a selected antibody applied as a coating to inert beads 70. The dispense member 62 has a construction generally similar to the seal fitting 48 of FIGS. 7-9, to include a central flow aperture 72 which is normally closed by a break-off nib 74 projecting into the lower chamber 64.

In use, a portion of a specimen-reagent mixture contained within the specimen chamber 46 of the housing cap 30 can be transferred through the outlet port 41 to the upper chamber 66 of the auxiliary housing member 60. In this regard, the reagent 20 mixed with the specimen on the swab tip 24 may be designed to perform an extraction or digestion function, in accordance with the test to be performed. At an appropriate time, the mixture can be transferred to the underlying chamber 66 by squeezing the housing cap to pressure force the fluid to flow through the port 41, or by squeezing and then releasing the auxiliary housing member 60 to draw the liquid by vacuum action. Within the chamber 66, the specimen-reagent mixture is contacted with the additional reagent therein. Thereafter, at the appropriate time, the test unit can be inverted as viewed in FIG. 11 and the break-off nib 74 severed from the dispense member 62 by deforming the lower region of the auxiliary housing member, followed by pressure-induced delivery of the additional reagent 68 through the aperture 72 to the chamber 66 to contact the treated specimen.

Another alternative embodiment of the invention is shown in FIG. 12, wherein a dispense member 62 of the type shown and described in FIGS. 10 and 11 is installed into the open end of a housing base 14. In this embodiment, the dispense member 62 again includes the central flow aperture 72 which is normally closed by the break-off nib 74. The nib 74 comprises a solid rod segment projecting into a reagent chamber 36 which contains a selected reagent or other medical fluid. The dispense member 62 provides a unitary component for normally sealing the housing cap 14 against reagent outflow, yet permitting controlled reagent dispensing upon severing the nib 74. More particularly, the base 14 can be deformed quickly and easily as described previously with respect to FIGS. 1-9 to bend and break the nib 74 to open the passage 72 to reagent flow. An outboard or nose end of the dispense member 62 conveniently defines a dropper tip 76 to form the dispensed liquid into discrete drops in response to controlled application of manual pressure to the housing base.

Figure 13:
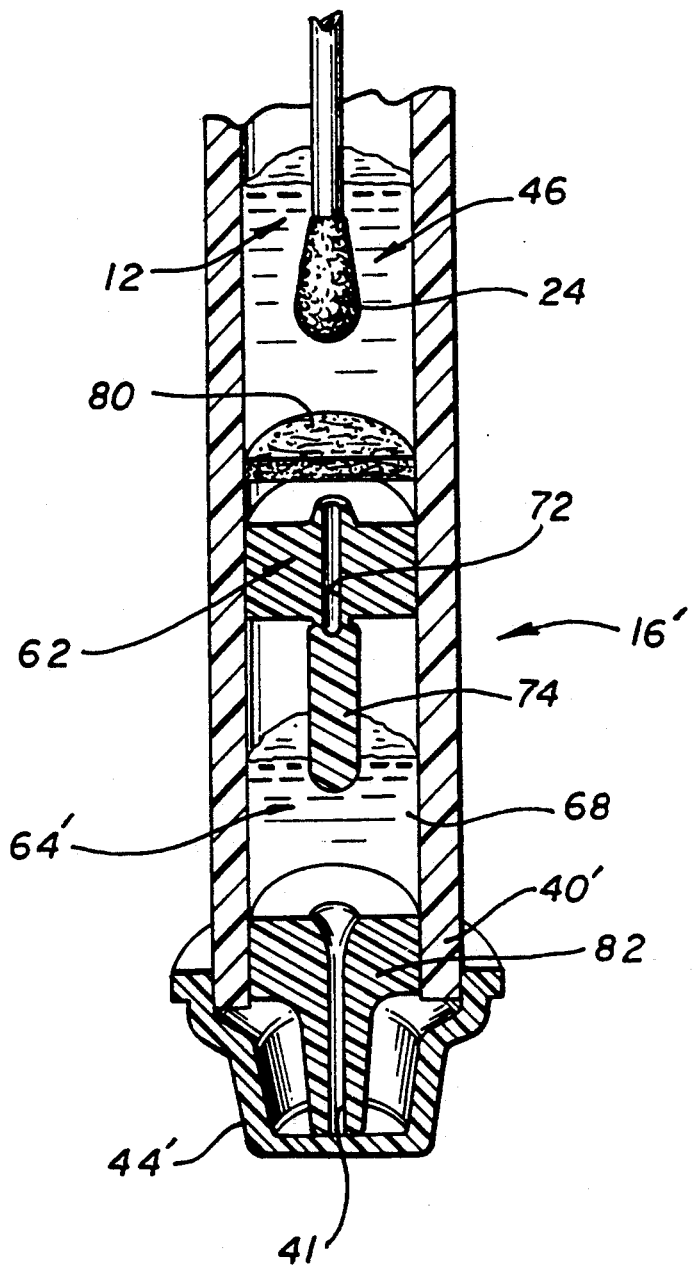
FIG. 13 is a fragmented perspective view showing still another alternative form of the invention.

FIG. 13 depicts still another form of the invention, wherein a modified housing cap 16' has an elongated and open lower end 40' protruding a substantial distance beyond or below the tip 24 of the swab 12 when the swab 12 is installed within the specimen chamber 46. In this regard, the modified cap 16' is designed to interfit with a housing base 14 of the type described in connection with FIGS. 1-9, to provide a mixed specimen and reagent within the specimen chamber 46.

The embodiment of FIG. 13 includes a dispense member 62 of the type described in FIGS. 10 and 11 but installed by press fitting or the like at an inset position within the lower end 40' of the housing cap. A filter 80 may also be provided within the cap 16' at a position between the dispense member 62 and the swab 12, if desired. The dispense member 62 again includes a central aperture 72 which is initially closed by a break-off nib 74. The nib 74 projects into a lower reagent chamber 64' formed within the lower end 40' of the housing cap 16'. A dropper tip 82 is pressed into the cap 16' at the lowermost end thereof, and an overcap 44' is normally mounted over the dropper tip 82 to close an outlet port 41' therein. With this construction, a second reagent 68 may be contained within the lower chamber 64'.

In use of the embodiment of FIG. 13, a mixed specimen chamber 46 can be mixed in turn with the additional reagent 68. Such additional mixing can be accomplished quickly and easily by deforming the lower region of the cap 16' to sever the nib 74, followed by appropriate deformation of the cap 16' to deliver one of the fluids through the aperture 72. That is, manipulation of the cap 16' as described previously herein can deliver the mixed specimen/reagent from the specimen chamber 46 to the lower chamber 64', or vice versa. Subsequent delivery of this resultant mixture from the test unit can be performed by removing the overcap 44' to permit dispensing through the dropper tip 82.

This invention thus provides several convenient and easily manipulated devices for quickly dispensing one or more reagents in a controlled manner, particularly with respect to delivering the reagent through a hollow swab shaft. The resilient housing component construction permits sufficient deformation to sever the break-off nib, and thereby permit reagent dispensing to the selected point of use.

A variety of further modifications and improvements to the present invention will be apparent to those skilled in the art. Accordingly, no limitation on the invention is intended by way of the foregoing description and accompanying drawings, except as set forth in appended claims.

What is claimed is:

1. A specimen test unit, comprising:
   a housing base defining a reagent chamber for receiving a selected flowable reagent, said housing base being formed from a resiliently deformable material;
   a swab member having a hollow swab shaft with a swab tip at a front end thereof and a break-off nib at a rear end thereof, said break-off nib preventing fluid inflow into a rear end of said hollow swab shaft; and
   mounting means for mounting said swab member on said housing base with said break-off nib disposed within said reagent chamber and said swab tip disposed outside said reagent chamber, said mounting means further including seal means for sealingly engaging and supporting said swab shaft at a position disposed between said break-off nib and said front end, said housing base being deformable to sever said break-off nib from said hollow swab shaft and thereby permit flow of said selected reagent within said reagent chamber through said hollow swab shaft to said swab tip, said break-off nib remaining within said reagent chamber subsequent to severing thereof from said swab shaft.

2. The specimen test unit of claim 1 further including a housing cap for removable mounting onto said housing base, said housing cap cooperating with said housing base to define a specimen chamber having said swab tip therein.

3. The specimen test unit of claim 1 wherein said break-off nib comprises a rod segment formed as a continuation of said hollow swab shaft and joined thereto at a score.

4. The specimen test unit of claim 3 wherein said break-off nib is formed integrally with said hollow swab shaft.

5. The specimen test unit of claim 1 wherein said seal means comprises a seal member on said housing base to define an aperture for sealed slide-fit reception of said swab shaft rear end.

6. The specimen test unit of claim 5 wherein said seal member comprises a seal collar formed integrally with said housing base.

7. The specimen test unit of claim 1 wherein said seal means comprises a seal fitting mounted on said housing base and defining a flow aperture therethrough, said seal fitting including means for supporting said swab shaft rear end with the hollow interior of said hollow swab shaft in flow communication with said flow aperture, and said break-off nib being positioned within said reagent chamber, said break-off nib normally preventing fluid inflow from said reagent chamber into said flow aperture, said housing base being deformable to break off said break-off nib and permit fluid flow from said reagent chamber to said flow aperture.

8. The specimen test unit of claim 7 further including an additional reagent within said flow aperture.

9. The specimen test unit of claim 7 wherein said break-off nib is formed integrally with said seal fitting.

10. The specimen test unit of claim 7 wherein said seal fitting is sized for press-fit sealed sliding reception into an open end of said housing base.

11. The specimen test unit of claim 2 wherein said housing base and said housing cap comprise blow molded plastic housing components.

12. The specimen test unit of claim 2 wherein said housing cap has an elongated shape with open opposite ends, one of the ends being adapted for slide-fit sealed connection with said housing base, and the other of said cap ends defining an outlet port for dispensing of fluid within said specimen chamber.

13. The specimen test unit of claim 12 further including an overcap for removable mounting onto said housing cap to close said outlet port.

14. The specimen test unit of claim 12 further including an auxiliary housing member on said housing cap to receive fluid dispensed from said housing cap through said outlet port, said auxiliary housing member defining at least one additional chamber having at least one additional reagent therein.

15. The specimen kit unit of claim 14 wherein said auxiliary housing member comprises an integral extension of said housing cap, and including a seal fitting having a flow passage therethrough and an additional break off nib at one end of said flow passage, said seal fitting separating said specimen chamber from said additional chamber.

16. The specimen test unit of claim 14 wherein said auxiliary housing member is formed from a resiliently deformable material and defines a pair of internal chambers having different reagents therein, said pair of internal chambers being separated by a seal fitting having a flow passage therethrough and an additional break-off nib at one end of said flow passage, said auxiliary housing being sufficiently deformable to permit said additional nib to be severed from said seal fitting to open said flow passage to fluid flow between said pair of internal chambers.

17. A specimen test unit, comprising:
a housing base defining a reagent chamber for receiving a selected flowable reagent, said housing base being formed from a resiliently deformable material; and
seal means on said housing base and defining a flow aperture leading from said reagent chamber to an exterior of said housing base, and seal means further including a break-off nib at one end of said flow aperture and disposed within said reagent chamber, said break-off nib preventing fluid flow from said reagent chamber through said flow aperture, said housing base being deformable to sever said break-off nib from said seal means and thereby open said flow aperture to fluid flow of the reagent from said reagent chamber, said break-off nib remaining within said reagent chamber subsequent to severing thereof from said seal means.

18. The specimen test unit of claim 17 wherein said seal means includes a drop former.

19. The specimen test unit of claim 17 wherein said seal means comprise a hollow shaft carried by said housing base, said hollow shaft having an inboard end of disposed within said reagent chamber and an outboard end disposed outside said reagent chamber, said break-off nib being mounted at said shaft inboard end.

20. The specimen test unit of claim 17 wherein said seal means comprises a seal fitting mounted on said housing base, and further including a hollow shaft carried by said seal fitting with one end of said shaft in flow communication with said flow aperture.

21. The specimen test unit of claim 17 further including a housing cap adapted for removable mounting onto said housing base to cover said flow aperture, at least one of said housing base and said housing cap being sufficiently deformable to sever said break-off nib from said seal means.

* * * * *